United States Patent [19]
Riede et al.

[11] 4,122,010
[45] Oct. 24, 1978

[54] APPARATUS FOR TREATING BLOOD

[75] Inventors: Gerhard Riede, Vellinge; Roland Johan Edvin Andersson, Bjarred, both of Sweden

[73] Assignee: Gambro AB, Lund, Sweden

[21] Appl. No.: 771,257

[22] Filed: Feb. 23, 1977

[30] Foreign Application Priority Data

Feb. 26, 1976 [SE] Sweden .......................... 024553/76

[51] Int. Cl.$^2$ ..................... B01D 35/00; B01D 35/14
[52] U.S. Cl. ................................. 210/90; 210/321 B
[58] Field of Search .................. 210/321 B, 138, 140, 210/186, 96 M, 23 F, 23 H, 23 R, 90, 85, 87

[56] References Cited
U.S. PATENT DOCUMENTS

| | | | |
|---|---|---|---|
| 3,352,779 | 11/1967 | Austin et al. | 210/23 F |
| 3,441,136 | 4/1969 | Serpass et al. | 210/96 M |
| 3,457,944 | 7/1969 | Cary et al. | 210/321 B |
| 3,474,904 | 10/1969 | Cary et al. | 210/321 B |
| 3,508,656 | 4/1970 | Serfass et al. | 210/90 |
| 3,515,275 | 6/1970 | Bowman | 210/22 |
| 3,563,381 | 2/1971 | Edelson | 210/321 |
| 3,744,636 | 7/1973 | Cammarmot | 210/321 B |

Primary Examiner—Frank A. Spear, Jr.
Assistant Examiner—E. Rollins Cross
Attorney, Agent, or Firm—Lerner, David, Littenberg & Samuel

[57] ABSTRACT

An apparatus for treating blood is disclosed which comprises a dialyzer for treating the blood with a treatment liquid and a circulating system which is operative to circulate the treatment liquid through the dialyzer. The circulating system comprises heating means for heating the treatment liquid to a predetermined treatment temperature and for heating the treatment liquid to a cleaning temperature such that when the treatment liquid is circulated through the circulating system at the cleaning temperature it will effect cleaning thereof. The circulating system further comprises actuating means for actuating the heating means to heat the treatment liquid to the cleaning temperature which means are only operative to actuate the heating means when the circulating system is in communication with the actuating means whereby the actuating means will not be operative when the circulating system is in communication with the dialyzer.

4 Claims, 1 Drawing Figure

U.S. Patent   Oct. 24, 1978   4,122,010
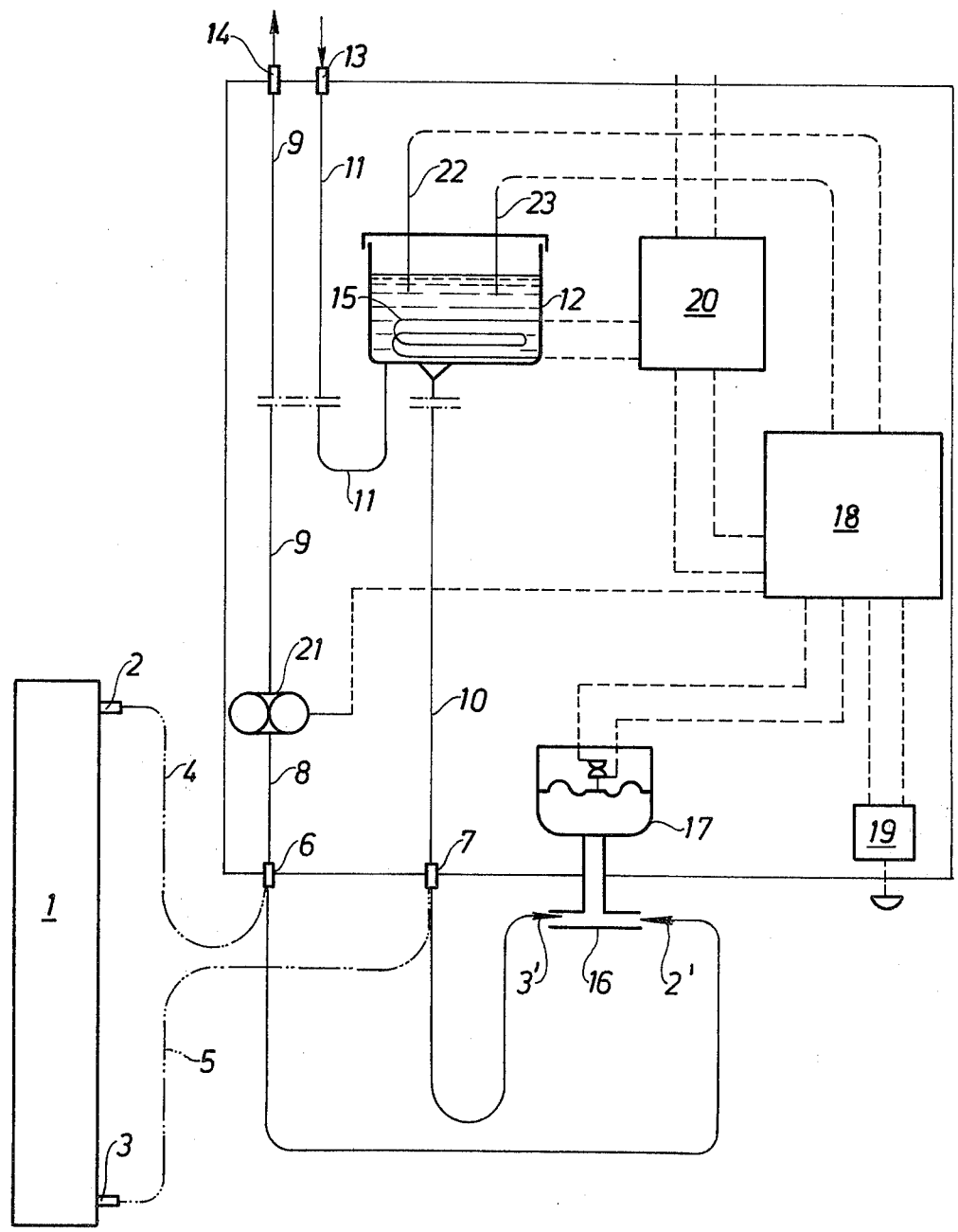

APPARATUS FOR TREATING BLOOD

BACKGROUND OF THE INVENTION

The treatment of blood or similarly perishable liquids by means of dialysis is well known. Typically, apparatus for such treatment comprises a dialyzer in combination with a closed circulating system for circulating a treatment liquid through the dialyzer to thereby effect dialysis of the blood. The closed system normally includes means for heating the treatment liquid to a temperature sufficient to effect the desired treatment or purification of the blood or other perishable liquid. Further, such heating means may be operative to heat the treatment liquid to above the treatment temperature such that the treatment liquid can be used to cleanse or sterilize the system when it is not in use.

When the blood treating apparatus as above described is in use and a patient's blood circulation system is connected directly to the dialyzer, it is essential that no heating of the treatment liquid to above the treatment temperature be permitted. Therefore, in order to avoid possible actuation of the heating element to heat the treatment liquid to the higher cleaning or sterilizing temperature, various safety devices have been employed. Such devices have included micro-switches which are connected to flexible tubes which usually connect the dialyzer to the closed circulating system. However, such micro-switches have been known to be acted upon by mechanical means other than those intended to operate such switches. Therefore, assurance that the treatment liquid would not be heated to above the treatment temperature is not sufficiently assured.

It is therefore an object of the present invention to provide an apparatus for treating blood or other perishable liquids which assures that the treatment liquid will not be heated to a cleaning or sterilizing temperature while the apparatus is in use and connected to a patient, thus providing the safety which has heretofore been lacking in prior art devices.

SUMMARY OF THE INVENTION

The present invention is directed to an apparatus for treating blood and other perishable liquids which comprises a dialyzer for treating the liquid with a treatment liquid by dialysis and a circulating system which is operative to circulate the treatment liquid through the dialyzer. The circulating system comprises heating means for heating the treatment liquid to a predetermined treatment temperature as well as for heating such treatment liquid to a cleaning or sterilizing temperature such that when the treatment liquid is circulated through the circulating system at such temperature, cleansing of the system will be effected. The circulating system further comprises actuating means for actuating the heating means to heat the treatment liquid to a cleaning or sterilizing temperature, such actuating means being operative to actuate the heating means only when the circulating system is connected to the actuating means instead of to the dialyzer. Thus, so long as the dialyzer is in communication with the circulating system, i.e., when the dialyzer is connected to a patient and being used, the heating means will not and cannot be actuated to heat the treatment liquid to above the treatment temperature.

The actuating means can comprise a pressure pick-up means which is operative to sense the pressure in the circulating system when the circulating system is brought into communication with the pressure pick-up means. The pressure pick-up means can be further operative to produce and transmit a signal to a signal sensing means, such as a micro-computer, which, in response thereto, can serve to actuate the heating means to effect heating of the treatment liquid to the desired cleaning temperature. Further, if desired, switch means can be included which are operative to provide still a second signal to the micro-computer such that actuation of the heating means will only occur when both the signal from the pressure pick-up and from the switch means are received.

DESCRIPTION OF DRAWING AND DETAILED DESCRIPTION

The invention herein can be better appreciated by reference to the following detailed description and drawing in which the FIGURE comprises a schematic illustration of the apparatus according to the present invention.

Referring now to the drawing, 1 designates a parallel flow-type dialyzer such as that disclosed, for example, in any of U.S. Pat. Nos. 3,411,630, 3,516,548, 3,734,298, and 3,837,496. During operation, the dialyzer is connected by flexible tubes, or the like, to a patient's blood circulation system in the manner described in any one of the aforementioned patents, the manner of such connection not being shown in the present drawing. Further, during operation the dialyzer 1 is connected to the circulating system for circulating treatment liquid by means of tubes 4 and 5 attached to the dialyzer by connecting nipples 2 and 3, and to the circulating system by coupling nipples 6 and 7. During treatment of a patient the dialyzer 1 together with the flexible tubes 4 and 5, the pipe lines 8, 9, 10 and 11, and a thermostat vessel 12 form a closed system for circulation of the treatment liquid through the dialyzer. Such closed system is connected to an inlet 13 and an outlet 14. During normal operation, a treatment liquid which normally consists of a salt solution, is circulated through the dialyzer while being maintained at a particular temperature in the manner set forth in the aforementioned patents.

Between treatments, it is often necessary to clean the various parts of the apparatus. This is effected by heating the treatment liquid to a cleaning or sterilizing temperature. Such heating takes place in the thermostat vessel 12 with the aid of heating element 15. For safety reasons, heating to such a cleaning or sterilizing temperature must not be possible when the dialyzer is coupled to a patient and to the system. Thus, in accordance with the present invention, actuating means are provided which are operative to actuate the heating element 15 to heat the treatment liquid up to a cleaning or sterilizing temperature only when the circulating system is disconnected from the dialyzer and placed in communication with the actuating means.

The actuating means comprise a pressure pick-up or vacuum relay 17 having a T-piece connector 16 for receiving flexible tube 4 and 5 by the nipples 2 and 3 which, in such position, are designated 2' and 3'. The actuating means further comprise micro-computer 18 which is adapted to receive a pressure signal from the pressure pick-up 17 and to in turn, in response to such signal, actuate the heating element 15 via the power supply 20, all shown schematically in the drawing. Additionally, if desired, switch 19 having open and closed positions can be provided and the micro-computer programmed such that the heating element 15 will not be actuated unless a signal from the switch 19 in its closed position and a signal from the pressure pick-up 17 are both received. Thus, in this embodiment extra safety is assured since only when the micro-computer receives both such signals will the element 15 be actuated via the power supply means 20.

As further shown in the drawing, if desired, a suction pump 21 can be connected to the micro-computer 18 such that the pump will be operative to effect circulation of the treatment liquid upon its being heated to a cleansing temperature in response to the signal received from the pressure pick-up 17. Where the pressure pick-up comprises a vacuum relay, the pump 21 can be connected to the line 10 rather than the line 9. Further, the apparatus can be provided with additional conventional elements such as thermometers, flowmeters, pressure gauges, etc. which can be connected in a manner known to those persons skilled in the art. As an example, elements 22 and 23, shown schematically in the drawing, represent temperature pick-ups for transmitting signals to the micro-computer 18 indicating, respectively, the treatment temperature and cleaning or sterilizing temperature of the treatment liquid.

While the invention has been described with a certain degree of particularity, it will be understood that the description was by way of example only and that numerous variations and modifications, as may become apparent to those of ordinary skill in the art, can be made without departing from the spirit and the scope of the invention as hereinafter claimed.

What is claimed is:

1. Apparatus for treating blood, comprising:
   a dialyzer for treating said blood by dialysis with a treatment liquid;
   a circulating system operative to circulate said treatment liquid through said dialyzer;
   said circulating system comprising heating means for heating said treatment liquid to a predetermined treatment temperature and for heating said treatment liquid to a cleaning temperature higher than said treatment temperature such that said treatment liquid when circulated through said circulating system at said cleaning temperature will effect cleaning thereof;
   actuating means for actuating said heating means to heat said treatment liquid to said cleaning temperature;
   communicating means for placing said circulating system in fluid communication with one of said dialyzer and said actuating means; and
   said actuating means being operative to actuate said heating means to heat said treatment liquid to said cleaning temperature only when said communicating means have been utilized to place said circulating system in fluid communication with said actuating means, whereby said actuating means cannot actuate said heating means to heat said treatment liquid to said cleaning temperature while said circulating system is in fluid communication with said dialyzer.

2. The apparatus of claim 1 wherein said actuating means comprises signal receiving means and pressure pick-up means for sensing the pressure in said circulating system when said circulating system is in fluid communication with said actuating means, said pressure pick-up neans being operative to produce and transmit a first signal to said signal receiving means in response to said pressure, said actuating means only being operative to actuate said heating means to heat said treatment liquid to said cleaning temperature when said first signal is received by said signal receiving means.

3. The apparatus of claim 2 wherein said actuating means further comprises switch means having an open and closed position, said switch means in said closed position being operative to produce and transmit a second signal to said signal receiving means, and said actuating means being operative to actuate said heating means to heat said treatment liquid to said cleaning temperature only when both said first and second signals are received by said signal receiving means.

4. The apparatus of claim 1 wherein said circulating system further comprises a pump for circulating said treatment liquid at said cleaning temperature, said pump being operative only when said circulating system is in fluid communication with said actuating means.

* * * * *